United States Patent [19]
Koakutsu et al.

[11] Patent Number: 6,090,630
[45] Date of Patent: Jul. 18, 2000

[54] METHOD AND APPARATUS FOR AUTOMATICALLY ANALYZING REACTION SOLUTIONS OF SAMPLES

[75] Inventors: Takahiro Koakutsu; Atsushi Takahashi, both of Mito, Japan

[73] Assignee: Hitachi, Ltd., Tokyo, Japan

[21] Appl. No.: 08/969,835

[22] Filed: Nov. 13, 1997

[30] Foreign Application Priority Data

Nov. 15, 1996  [JP]  Japan ................................ 8-304709

[51] Int. Cl.[7] .................................................. G01N 35/00
[52] U.S. Cl. .............................. 436/50; 436/43; 422/63; 422/67
[58] Field of Search ................... 436/43, 49, 50, 436/180; 422/63, 67, 81; 364/528.01

[56] References Cited

U.S. PATENT DOCUMENTS

| | | |
|---|---|---|
| 4,451,433 | 5/1984 | Yamashita et al. . |
| 4,754,414 | 6/1988 | Gocho . |
| 5,254,311 | 10/1993 | Ushikubo ................................. 422/81 |
| 5,314,825 | 5/1994 | Weyrauch et al. . |
| 5,719,059 | 2/1998 | Mimura et al. ........................... 435/50 |

FOREIGN PATENT DOCUMENTS

| | | |
|---|---|---|
| 510 686 | 4/1991 | European Pat. Off. . |
| 732 591 | 9/1996 | European Pat. Off. . |
| 197 01 505 | 7/1997 | Germany . |

*Primary Examiner*—Long V. Le
*Attorney, Agent, or Firm*—Beall Law Offices

[57] ABSTRACT

When an operator touches a reagent interruption key during a continuous analyzing operation of samples in an operation state, the succeeding sampling operation is temporarily suspended and a reagent interruption screen is displayed on a screen of a CRT. A reagent delivery operation as to pipetted samples and a light-measurement operation as to the reaction solution are continued. A waiting time period until an operation for exchanging a reagent bottle can be started is displayed on the screen. When the waiting time period becomes zero minutes, an operator touches an execution key. Then, a screen representing readiness for exchanging a reagent bottle is displayed and an analyzing apparatus is placed in a reagent exchange waiting state for waiting for exchanging the reagent bottle. When an operator touches the execution key after exchanging the reagent bottle, the analysis apparatus reads bar codes o the reagent bottles on the reagent disks and registers the reagent information. Thereafter, an operation screen is displayed and the analysis apparatus is restored to an operation state thereby to continue the analysis operation of the samples.

7 Claims, 5 Drawing Sheets

METHOD AND APPARATUS FOR AUTOMATICALLY ANALYZING REACTION SOLUTIONS OF SAMPLES

BACKGROUND OF THE INVENTION

The present invention relates to a method and an, apparatus for automatically analyzing reaction solutions formed by mixing samples with reagents respectively corresponding to analysis items.

In the conventional automatic analyzing apparatus, as disclosed in U.S. Pat. No. 4,451,433, for example, reagents are prepared before analyzing samples in correspondence to the number of the samples and the number of analysis items required for the measurement, and then the analysis of the samples is started. In such a conventional apparatus, when a sample required to be analyzed immediately or a sample to be analyzed normally is added or when a measured value of a sample having been analyzed is an abnormal value, it is required to analyze again the same sample already analyzed. If the number of samples to be analyzed exceeds the predetermined number of the samples which was estimated in advance due to an unpredictable factor, there arises a problem that the amounts of the reagents become insufficient for the analysis.

Since not all the reagents become insufficient in their amounts, the analysis can be continued as to some analysis items corresponding to the sufficient reagent(s). However, as to the insufficient reagent, the analysis result of the analysis item associated with such a reagent becomes insufficient since the reagent cannot be added during the analysis operation. Accordingly, in this case, an operator exchanges a reagent bottle associated with the analysis item having insufficient remaining amounts of reagent for a new one, then selects the sample(s) corresponding to the analysis item having not been analyzed due to the shortage of the reagent, and analyzes the sample(s) again.

When the automatic analyzing apparatus is in an operation state for performing a sample delivering operation, a reagent delivering operation and a light-measurement operation after starting the analysis of samples, a disk (hereinafter referred to as a reagent disk) mounting a reagent pipetting unit and reagent bottles thereon is operated. Accordingly, a reagent bottle cannot be exchanged during the analysis operation even if the remaining amount of the reagent bottle which has been provided before the analysis operation becomes small.

Thus, when the remaining amount of a reagent within a reagent bottle for a particular analysis item becomes small and the analysis using the reagent has not been completed, an operator is required to push a sampling stop key thereby to shift the automatic analyzing apparatus to a standby state, and thereafter to register a new reagent bottle.

In this manner, there arises a problem that the efficiency for analyzing samples is degraded since an operator is required to perform such an additional troublesome analysis operation and to analyze the same samples twice.

Further, in a case where, although an amount of the reagent was sufficient for analyzing a predetermined number of samples, a sample(s) to be analyzed is added or an analysis item(s) as to a sample(s) that has already been analyzed once is required to be analyzed again (that is, when a measured value of an analysis item for a sample that has been analyzed is an abnormal value, the analysis is performed again as to the same analysis item of the same sample so as to verify the correct value), it is required to shift the automatic analyzing apparatus to the standby state from a present operation state or a sampling stop state thereby to register a new reagent bottle.

SUMMARY OF THE INVENTION

An object of the present invention is to provide a method and an apparatus for automatically analyzing reaction solutions of samples, which is able to exchange a reagent bottle without shifting the automatically analyzing apparatus to a standby state when it is found during the continuous analyzing operation that an amount of at least one reagent corresponding to one analysis item is insufficient and a reagent bottle of such reagent is required to be exchanged for a new one.

According to an aspect of the present invention, there is provided an analyzing method using an automatic analyzing apparatus in which samples and reagents are delivered into a series of reaction containers on a reaction line to form reaction solutions within the reaction containers, and light measurement is performed as to reaction solutions with respect to predetermined analysis items, the method comprising the steps of:

(a) shifting the automatic analyzing apparatus to an operation state from a standby state, and performing a sample delivery operation, a reagent delivery operation and a light-measurement operation of a reaction solution during the operation state;

(b) in response to a request for exchanging a reagent bottle for a new one occurred during the operation state, displaying an interruption screen on a display unit, temporarily suspending the sample delivery operation, and continuing the reagent delivery operation until necessary amounts of reagents are added to the respective samples which have been delivered into the reaction containers on the reaction line;

(c) displaying on the display unit time information representing a time period required for completing delivery of the reagent in step (b); and (d) representing on the display unit that the exchange of the reagent bottle indicated by the request is possible when delivery of the reagent in step (b) is completed.

According to a preferred embodiment of the present invention, succeeding step (c), the automatic analyzing apparatus is placed in a reagent exchange waiting state for waiting for exchanging the reagent bottle indicated by the request. The light-measurement operation is continued even in the reagent exchange waiting state. Further, information of the reagent of the new reagent bottle such as analysis item information or information representing a kind of the new reagent is registered in a memory of the control unit in response to input of a signal representing completion of the exchange for the new reagent bottle during the reagent exchange waiting state.

Further, according to a preferred embodiment of the present invention, when the temporary suspension of the sample delivery operation and the reagent delivery operation is canceled after the information of the new reagent bottle is registered, the automatic analyzing apparatus returns to the operation state. Further, when an instruction to cancel the interruption is issued after the request for exchanging in step (b) or during the reagent exchange waiting state, the automatically analyzing apparatus returns to the operation state.

DESCRIPTION OF THE PREFERRED EMBODIMENTS

First, the arrangement of the automatic analyzing apparatus to which the present invention is applied will be explained with reference to FIG. 2.

Figure 2:
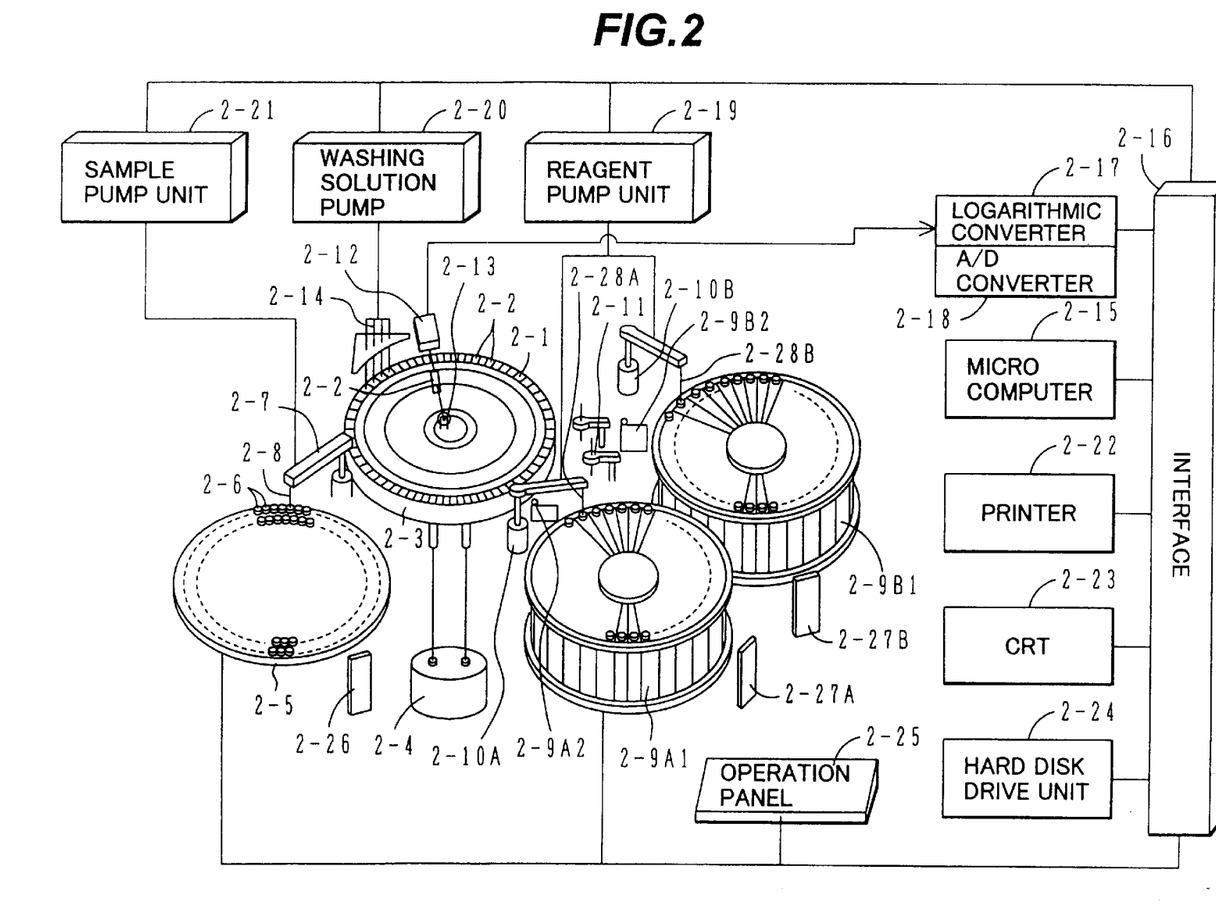
FIG. 2 is a schematic diagram showing an arrangement of the automatic analyzing apparatus to which the present invention is applied.

In FIG. 2, reaction containers 2-2 are provided on the outer periphery of a reaction disk 2-1. The reaction disk 2-1 is entirely kept at a predetermined temperature by an incubation bath 2-3. A constant-temperature water supplying unit 2-4 supplies water of constant temperature (e.g., 37° C.) to the incubation bath 2-3.

A multiplicity of sample cups 2-6 are provided on a sample disk unit 2-5. A sample within each of the sample cups 2-6 is sucked by a predetermined amount into a nozzle 2-8 mounted at a movable arm of a sample pipetting unit 2-7, and then the sucked sample is delivered into the reaction container 2-2 positioned at a sample delivery position. Identification information of each of the sample cups 2-6 is read by a bar code reader 2-26. In each of two reagent disks 2-9A1 and 2-9B1, there are set a multiplicity of reagent bottles, each pasted on its outer wall with a label having reagent information represented by a bar code. Bar code readers 2-27A and 2-27B are disposed in correspondence to the reagent disks 2-9A1 and 2-9B1, respectively. When new reagent bottles are set in the reagent disk, the reagent information of the respective new reagent bottles is read by the corresponding bar code readers and registered in a hard disk drive unit 2-24 serving as a memory device, together with the information of the setting position of the new reagent bottle on the reagent disk.

A reagent pipetting unit 2-10A and a second reagent pipetting unit 2-10B are provided in correspondence with the reagent disks 2-9A1 and 2-9B1, respectively. Reagent probes 2-28A and 2-28B are provided for pipetting reagents corresponding to the analysis items into the reagent bottles. Washing solution bottles 2-9A2 and 2-9B2 each containing therein a washing solution for supplementarily washing the contamination within the reaction containers 2-2 are provided between the reaction disk 2-1 and the reagent disks 2-9A1 and 2-9B1, respectively. The washing solution is delivered into the reaction containers 2-2 by the reagent probes 2-28A and 2-28B, and then the solution in the reagent containers is discharged into an exhausting unit (not shown). Since the washing solution is sucked into the reagent probes 2-28A and 2-28B from the washing solution bottles and then discharged into the exhausting unit, the contamination within the probes can also be eliminated.

At the outside of the reagent disks 2-9A1 and 2-9B1, there are provided stirrers 2-11 for stirring the mixture within the reaction containers 2-2 in the vicinity of the reaction disk 2-1. The reaction container 2-2 containing therein a subject being subjected to the light measurement is disposed between a multi-wavelength photometer 2-12 and a light source lamp 2-13. A reference numeral 2-14 depicts a washing unit for washing the reaction containers 2-2.

Next, an explanation will be made as to a control system and a signal processing system of the automatic analyzing apparatus. A microcomputer 2-15 includes a clock unit and controls the operation of the respective units. A reference numeral 2-16 depicts an interface, 2-17 a logarithmic (log) converter, 2-18 an analog-to-digital (A/D) converter, 2-19 a reagent pump unit, 2-20 a washing solution pump and 2-21 a sample pump unit.

A reference numeral 2-22 depicts a printer for printing the analyzing results, etc., 2-23 a cathode ray tube (CRT) for displaying a screen, 2-24 the hard disk drive unit serving as a memory device, and 2-25 an operation panel (that is, a key board or a pointing device such as a touch screen, a mouse or the like).

In the arrangement shown in FIG. 2, the samples contained in the sample cups 2-6 are sequentially delivered into the reaction containers 2-2 on the reaction disk 2-1 by using the nozzle 2-8 of the sample pipetting unit 2-7 in accordance with the analysis parameters stored in a memory of the microcomputer 2-15 which have been inputted in advance through the operation panel 2-25.

Then, the reaction containers 2-2 in which the samples have been delivered are sequentially transferred to a reagent delivery position in accordance with the counterclockwise rotation of the reaction disk 2-1. Thereafter, the reagents are delivered by a predetermined amount into the reaction containers 2-2, in which the samples have been delivered, by using the probes 2-28A and 2-28B of the reagent pipetting units 2-10A and 2-10B, respectively, in accordance with the measuring conditions according to the respective analysis items (the analysis parameters) stored in the microcomputer 2-15.

Then, the mixture of the sample and the reagent within each of the reaction containers 2-2 is stirred and mixed so as to be homogeneous. When the reaction container 2-2 crosses a light measuring position, an absorbance of the mixture within the reaction container 2-2 is measured by the multi-wavelength photometer 2-12. The absorbance thus measured is taken into the microcomputer 2-15 through the logarithmic converter 2-17, the A/D converter 2-18 and the interface 2-16. The absorbance is converted into concentration data on the basis of a calibration curve prepared from the absorbance of the standard sample solution which has been measured in advance by the analysis method designated for each analysis item. The concentration data thus measured for the respective analysis items are outputted to the printer 2-22 and/or the screen of the CRT 2-23.

In order to make the automatic analyzing apparatus execute the aforesaid operations, an operator sets the various parameters required for measuring all the analysis items, registers the samples and confirms the results of the analysis with reference to the screen of the CRT 2-23.

Figure 3:
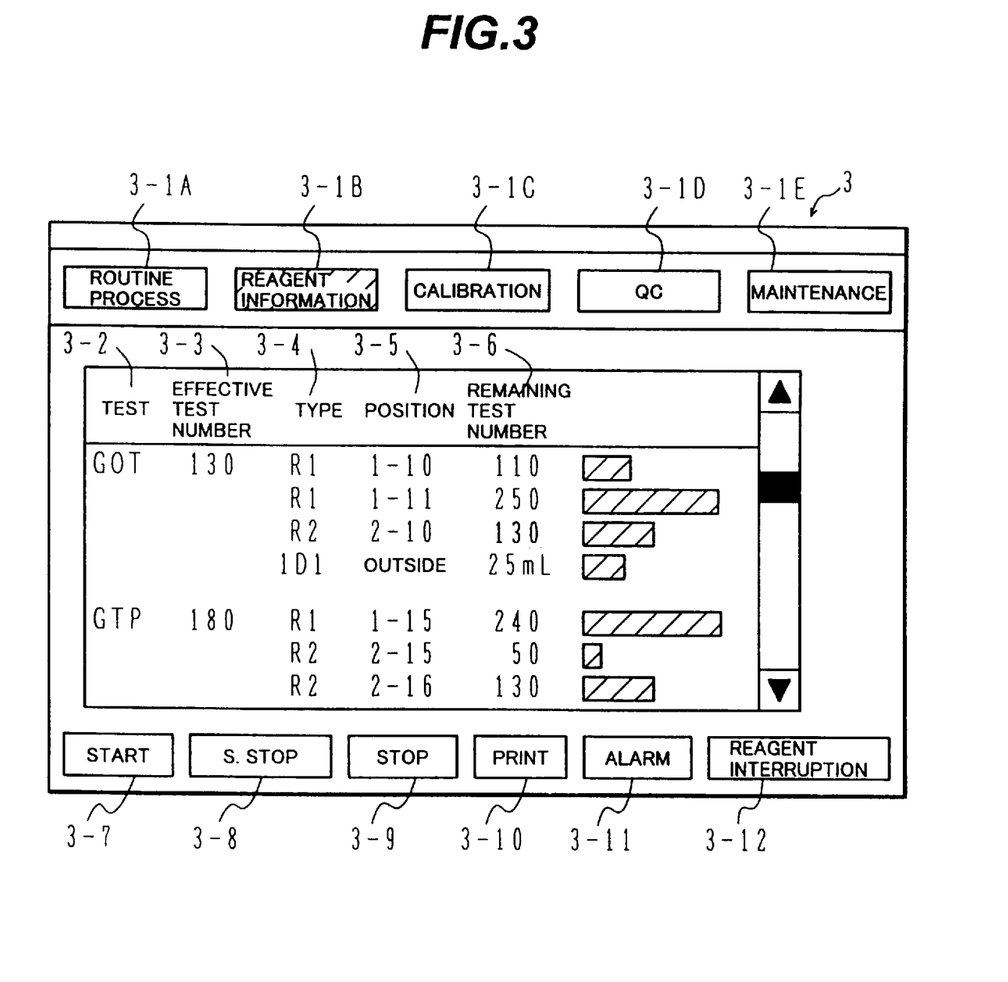
FIG. 3 is a diagram showing an example of a reagent information screen displayed on a CRT of the automatic analyzing apparatus in FIG. 2.

FIG. 3 shows an example of the screen for the reagent information displayed on the screen of the CRT 2-23. Reference numerals 3-1A, 3-1B, 3-1C, 3-1D and 3-1E in FIG. 3 depict peculiar display sections for selecting functions of the automatic analyzing apparatus. These display sections are arranged to display menus associated with the functions, respectively.

An operator in advance measures parameters and data necessary for the measurement by using the display sections "MAINTENANCE", CALIBRATION", "QC" corresponding to the functions such as the maintenance, calibration, QC or the like, respectively, and requests the analysis items necessary for the respective samples by using the display section "ROUTINE PROCESS" corresponding to the function of the routine process. Further, in the usual operation, an operator confirms whether or not there remains sufficient amount of reagents as to the analysis items to be analyzed from now by using the display section "REAGENT INFORMATION" corresponding to the function of the reagent information.

The display section "TEST" 3-2 on the screen 3 displays the analysis items. The analysis items displayed on this display section correspond to the analysis items of the parameters set by using the display section "MAINTENANCE". The display section "EFFECTIVE TEST NUMBER" 3-3 displays the smaller one of the remaining amounts of the reagents used for each of the respective analysis items. For example, as to the analysis item "GOT", the display section "EFFECTIVE TEST NUMBER" 3-3 displays the smaller one of the remaining amounts between the first reagent R1 and the second reagent R2. In this example, two bottles of the first reagent R1 are set and the remaining amount thereof corresponds to an amount of 360 tests for the analysis item "GOT", whereas the remaining amount of the second reagent R2 corresponds to an amount of 130 tests for the analysis item "GOT".

According to such a display, an operator can confirm that the reagents for the analysis item "GOT" are ensured by an amount corresponding to 130 tests (corresponds to 130 samples) in total. The display section "TYPE" 3-4 displays the types of the reagents, that is, the first reagent R1 and the second reagent R2, used in the associated analysis items. The display section "POSITION" 3-5 displays setting positions where the reagent bottles are positioned. The display section "REMAINING TEST NUMBER" 3-6 displays the remaining amounts of the respective reagent bottles, both as numerical values and as bar graphs so that an operator is able to understand the remaining values at a glance. On the screen 3, a reference numeral 3-7 depicts a start key, 3-8 a sampling stop key, 3-9 a stop key, 3-10 a print key, 3-11 an alarm key and 3-12 a reagent interruption key.

The operation of the automatic analyzing apparatus according to the first embodiment of the present invention will be explained with reference to the flow chart shown in FIG. 1.

First, when the automatic analyzing apparatus is in a standby state (step 1-1), an operator operates the operation panel 2-25 to display the display screen 3 shown in FIG. 3 on the CRT thereby to confirm the remaining amounts of the respective reagents. Then, the operator touches the start key 3-7 to place the automatic analyzing apparatus in an operation state (step 1-2), whereby the automatic analyzing apparatus starts the continuous analyzing operation of the samples. When the sampling operation as to all the samples set on the sample disk unit 2-5 is completed, the automatic analyzing apparatus is automatically placed in a sampling stop state (step 1-3) and then stops the operation thereof (step 1-4) and the process thereof returns to the standby state (step 1-1). Data representing the results of the measurement as to the analysis items measured during the aforesaid period from the step 1-1 to the step 1-4 are outputted to the printer 2-22 or the CRT 2-23.

When there arises a case during the operation that a new sample to be measured is added or the sample having been measured once is required to be analyzed again, if the remaining amount of the reagent within the reagent bottle necessary for measuring such a sample is insufficient, the operator is able to exchange the reagent bottle for a new one without waiting for the automatic analyzing apparatus to be in the standby state.

Figure 4:
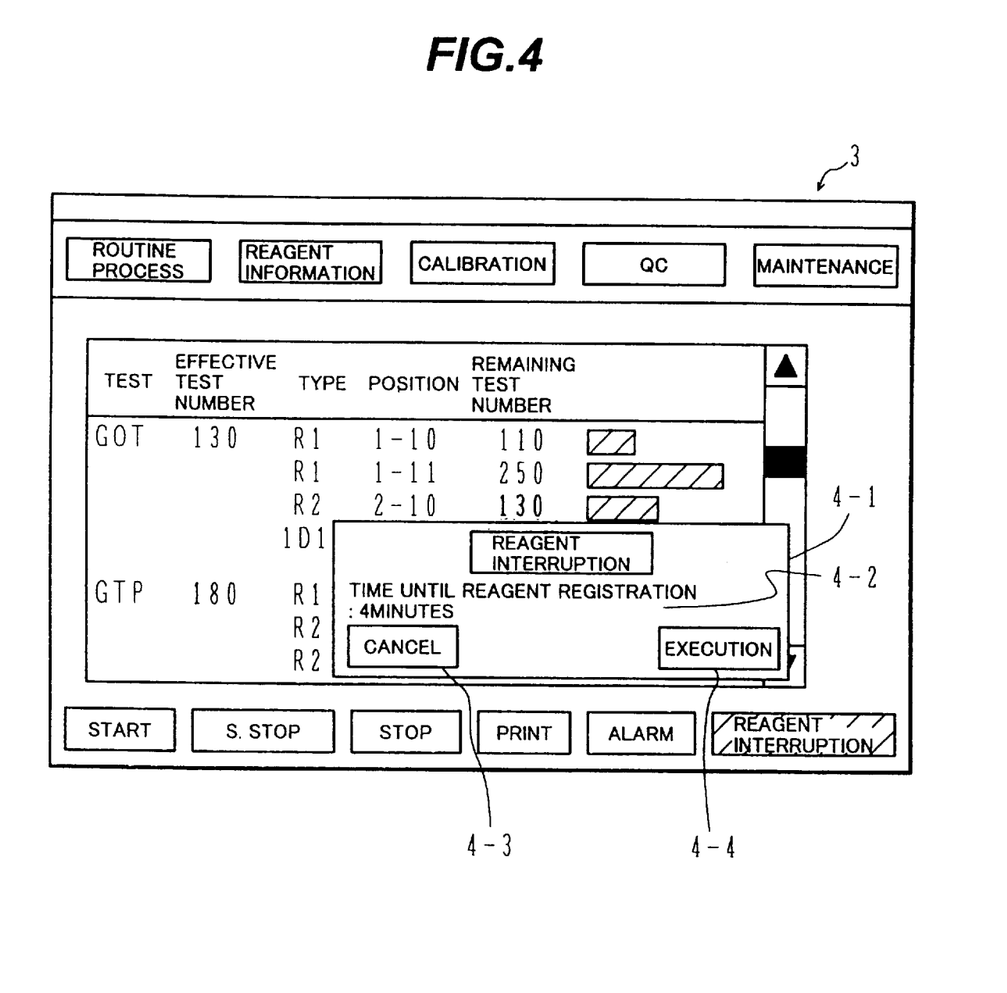
FIG. 4 is a diagram showing an example of a reagent interruption screen.

In other words, in the present embodiment, in a case where the remaining amount of the reagent within the reagent bottle becomes small during the operation, when the operator touches the reagent interruption key 3-12 on the display screen 3 shown in FIG. 3 so as to request the reagent interruption, the automatic analyzing apparatus is placed in a "reagent interruption" input state (step 1-5). Thus, a part of the analysis operation is temporarily stopped or suspended, that is, the automatic analyzing apparatus is placed in a sampling stop state capable of restarting the operation (step 1-6). Succeedingly, a reagent interruption screen (a small screen of a window like configuration) is displayed within the "reagent information" screen 3, as shown in FIG. 4 (step 1-6A).

In this case, the automatic analyzing apparatus is placed in the sampling stop state, wherein the nozzle 2-8 stops the sampling operation of the samples after the reagent interruption, and the next process is stopped until the delivery of the reagents corresponding to the analysis items of the samples that have been sampled heretofore is completed. A time period required until the delivery of the reagent from the reagent bottle corresponding to the final analysis item is calculated in accordance with the scheduling information as to the analysis conditions of all the analysis items, and the calculated time period is displayed on the reagent interruption screen 4-1 as a time period 4-2 required until the reagent registration. This time period 4-2 is continuously counted down until the time period becomes 0 minutes. In other words, the reagent interruption screen 4-1 displays waiting time information representing a time period from the reagent interruption to a state where the exchanging operation of the reagent bottle by the operator becomes possible.

Figure 5:
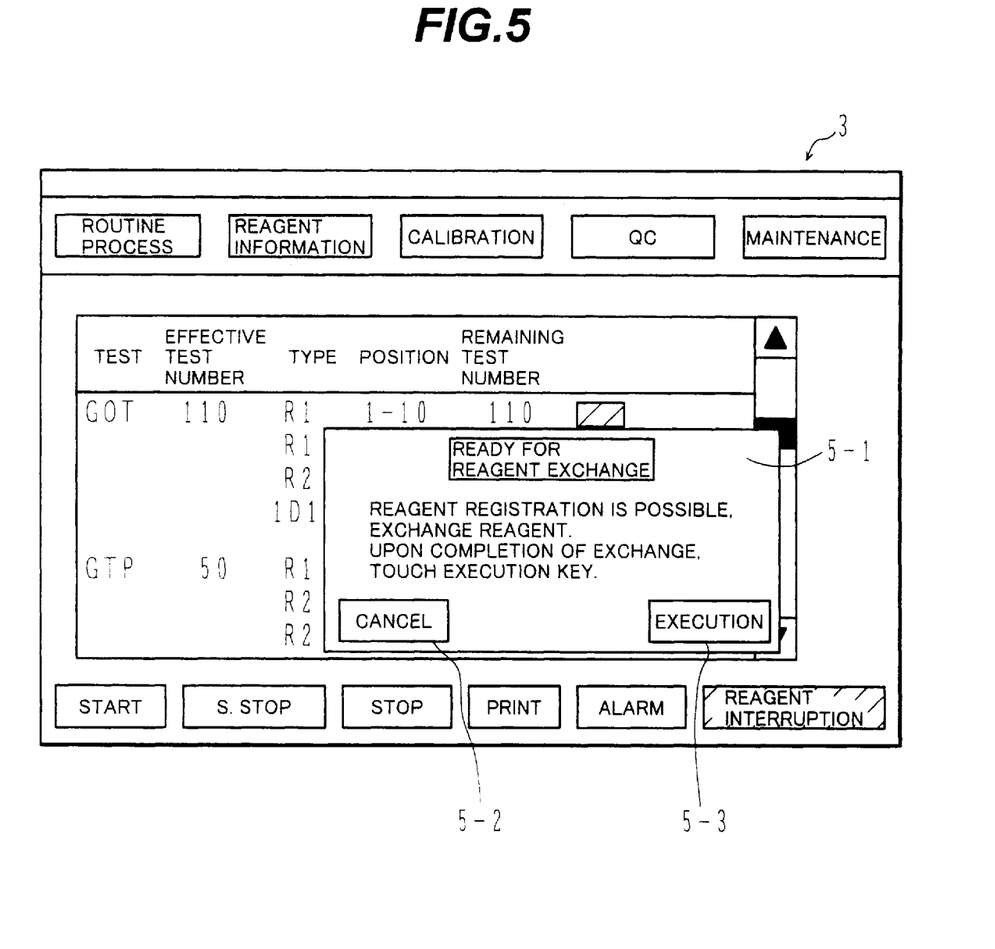
FIG. 5 is a diagram showing an example of a screen representing readiness for exchanging a reagent bottle.

The microcomputer 2-15 serving as a control unit determines whether the aforesaid required time period, that is, a waiting time period becomes 0 minutes or a cancel key 4-3 is touched (step 1-7). When the cancel key 4-3 is touched, the process returns to the operation state (step 1-2). In contrast, when the waiting time period becomes 0 minutes, determination is made whether or not an execution key 4-4 is touched (step 1-a). If it is determined that the execution key 4-4 is touched, a "ready for reagent exchange" screen 5-1 ( a small display screen of a window like configuration) is displayed within the reagent information screen 3 as shown in FIG. 5 to notify the operator that the exchanging operation of the reagent bottle is possible (step 1-7B). Then, the process proceeds to a state waiting for exchanging the reagent (step 1-8). During this period, both the rotating operation of the reaction disk 2-1 and the light-measuring operation of the multi-wavelength photometer 2-12 are continued, thereby to execute the analyzing operation of the reaction solution.

It is determined by the microcomputer 2-15 whether or not the operator has exchanged the old reagent bottle(s) of the reagent disk 2-9A1 and/or the reagent disk 2-9B1 for a new reagent bottle(s) and the registration of the reagent bottle is possible (step 1-9). In this case, if a cancel key 5-2 is touched, the process returns to the step 1-2. When the operator touches an execution key 5-3 after exchanging the reagent bottle (step 1-10), both the reagent disk 2-9A1 for the first reagent R1 and the reagent disk 2-9B1 for the second reagent R2 are rotated. Then, the bar codes of the reagent bottles of the respective reagent disks are read, and the kinds and the setting positions of the respective reagents thus read are registered, that is, updated. The registration state of the reagents thus updated is displayed on the reagent information screen 3 shown in FIG. 3 (step 1-11).

Then, it is determined whether or not the registration of the reagents is completed (step 1-12). If it is determined that the registration of the reagents is completed, the temporary suspended state of both the sample delivery operation and the reagent delivery operation is canceled, the operation screen is then displayed on the CRT (step 1-13) and the process returns to the step 1-2. Thereafter, the sampling operation is restarted by the sample pipetting unit 2-7 as to the samples having not been sampled yet thereby to continue the continuous analysis operation.

As described above, according to the first embodiment of the present invention, when there arises a need for exchanging a reagent bottle, the reagent exchange operation can be executed without restoring the automatic analyzing apparatus to the standby state by placing the apparatus in the "reagent interruption" input state. In this case, it is possible to automatically set and display the exchanging timing of the reagent, to automatically register a new reagent thus exchanged, and thereafter to automatic restore the automatically analyzing apparatus to the operation state.

While, in the aforesaid embodiment, both the reagent interruption screen 4-1 and the "ready for reagent exchange" screen 5-1 are displayed as a part of the reagent information screen 3. Each of the screens 4-1 and 5-1 may be displayed on the entire screen of the CRT.

Further, while, in the aforesaid embodiment, among all the functions displayed on the screen 3 in FIG. 3, the operation of the remaining functions other than the reagent information is limited, it is possible to arrange the apparatus to operate only the selected function(s). For example, the functions designated by the stop key 3-9 and the alarm key 3-11 may be made operable even in the reagent interruption state.

The explanation will be made as to the second embodiment of the present invention.

The reagents used in the analysis are sucked into the reagent probes 2-28B and 2-28A from the reagent bottles disposed at the reagent disks 2-9B1 and 2-9A1, respectively. If the washing solution bottles are disposed within the reagent disks 2-9B1 and 2-9A1, the reagent probes 2-28B and 2-28A can not be operated in the reagent registration state because the reagent disks 2-9B1 and 2-9A1 are being operated. Accordingly, the carry over washing process due to the contamination within the reaction containers 2-2 of the reaction disk 2-1 cannot be performed, for example.

In contrast, as shown in FIG. 2, in the case where the washing solution bottles 2-9B2 and 2-9A2 are disposed outside the reagent disks 2-9B1 and 2-9A1 and disposed along the moving loci of the reagent probes 2-28B and 2-28A, respectively, the carry over washing process etc. can be performed by operating the reagent probes 2-28B and 2-28A between the reaction disk 2-1 and the washing solution bottles, even in the reagent registration state in which the reagent disks 2-9B1 and 2-9A1 are operated.

The second embodiment is arranged in a manner that, when the "reagent interruption" input state is executed and the addition of the reagents as to the pipetted samples is completed, the reagent registration operation is executed in parallel to the washing operation of the reaction containers using the reagent probes 2-28B and 2-28A or the washing operation of the reagent probes themselves.

Figure 1:
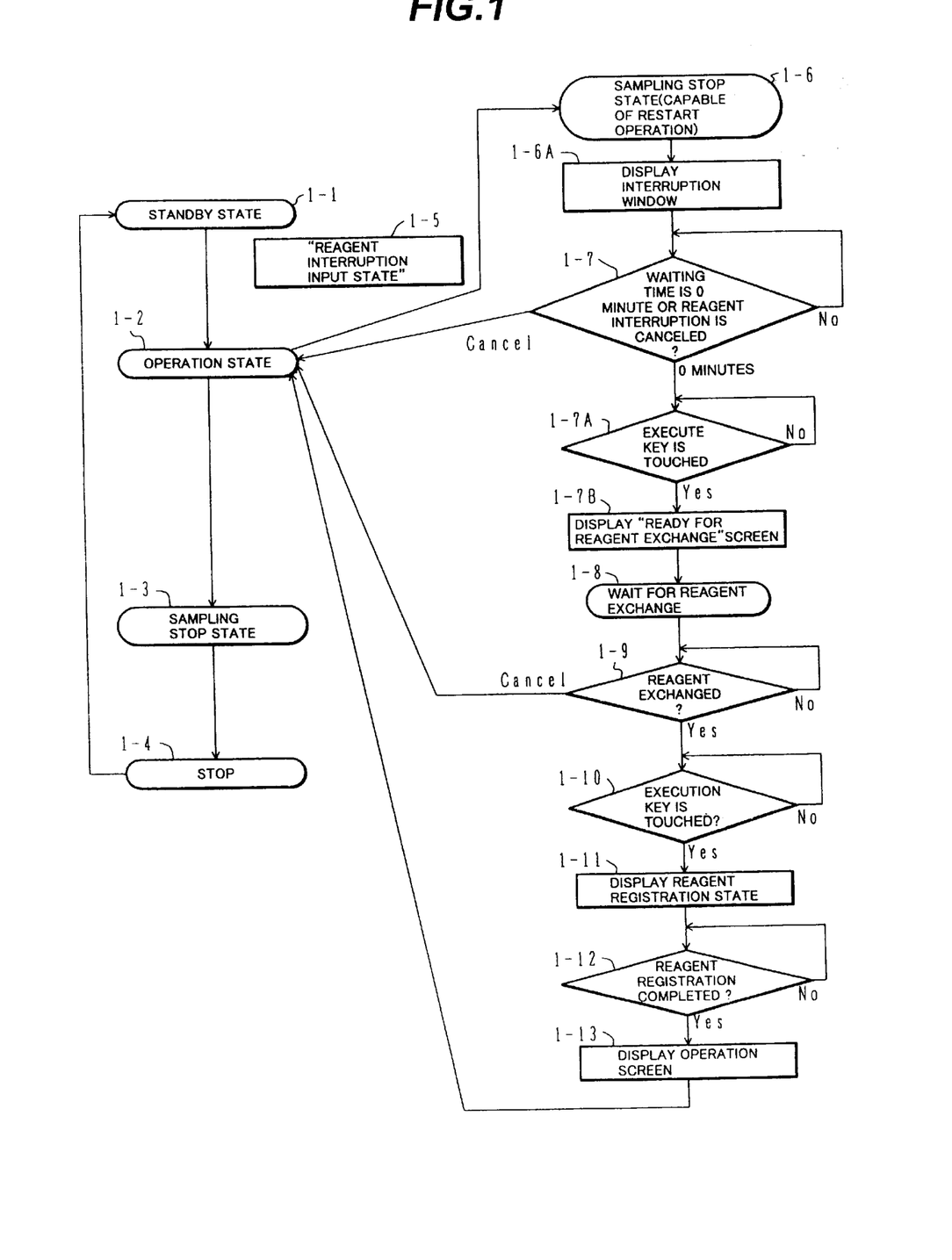
FIG. 1 is a diagram showing a flow chart for explaining the operation of an automatic analyzing apparatus of FIG. 2.

More concretely in the flowchart shown in FIG. 1, a step for executing the washing operation using the reagent probes 2-28A and 2-28B is inserted after the step 1-7. When the cancel key 4-3 or 5-2 is touched or the reagent registration process is completed during the washing operation, the process returns to the step 1-2. The arrangement of the remaining portions of the second embodiment is same as that of the first embodiment, and so the explanation and the drawings thereof are omitted.

The second embodiment of the present invention is able to attain the same technical advantages as those of the first embodiment, and further able to execute the washing operation of the reaction containers or the reagent probes during the reagent interruption state.

While, in the aforesaid embodiments, the samples are pipetted into the reaction containers before pipetting the reagents, the automatic analyzing apparatus may be arranged to pipette the reagents before pipetting the samples.

What is claimed is:

1. An analyzing method using an automatic analyzing apparatus in which samples and reagents are delivered into a series of reaction containers on a reaction line to form reaction solutions within the reaction containers, and light measurement is performed as to reaction solutions with respect to predetermined analysis items, said method comprising the steps of:

(a) shifting said automatic analyzing apparatus to an operation state from a standby state, and performing a sample delivery operation, a reagent delivery operation and a light-measurement operation of a reaction solution during the operation state;

(b) displaying, through a reagent information screen displayed on a display unit, an interruption screen on said display unit when an interruption operation is required to exchange a reagent bottle, temporarily suspending said sample delivery operation, and continuing said reagent delivery operation until necessary kinds of reagents are added to said samples which have been already delivered into said reaction containers on the reaction line;

(c) displaying time information on said display unit, said time information representing a waiting time period required for completing delivery of all reagents in said step (b);

(d) displaying a representation on said display unit that the exchange of said reagent bottle indicated by said interruption screen is possible when delivery of all reagents in said step (b) is completed;

(e) maintaining said automatic analyzing apparatus in the condition such that the exchange of said reagent bottle is possible, succeeding to said step (d), until completion of said exchange is required; and (f) continuing light measurement for said reaction solutions on said reaction line while said automatic analyzing apparatus is maintained in the condition according to step (e).

2. An analyzing method according to claim 1, wherein information of said new reagent bottle is registered in a memory in response to input of a signal representing completion of the exchange for said new reagent bottle during said waiting time period.

3. An analyzing method according to claim 2, wherein, when said temporary suspension of said sample delivery operation and said reagent delivery operation are canceled after said information of said new reagent bottle is registered, said automatically analyzing apparatus returns to said operation state.

4. An analyzing method according to claim 1, wherein, when an instruction to cancel said interruption is issued after said step (b) or during said waiting time period, said automatically analyzing apparatus returns to said operation state.

5. An automatic analyzing apparatus including a reaction line having a series of reaction containers thereon, a sample supply unit for delivering samples to be analyzed into reaction containers on said reaction line, a reagent supply unit for delivering reagents according to analysis items into said reaction containers on said reaction line, and a light-measurement unit for performing light measurement as to reaction solutions within said reaction containers on said reaction line, said automatic analyzing apparatus further comprising:

- a display unit for displaying information relating to said reagents on a screen when a sample delivery operation, a reagent delivery operation and a light-measurement operation of a reaction solution are operated by said automatic analyzing apparatus;
- a first operation key for entering an interruption request for exchanging a reagent bottle when said sample delivery operation, said reagent delivery operation and said light-measurement operation of said reaction solution are operated by said automatic analyzing apparatus, said first operation key being displayed on a screen of said display unit;
- a control unit for controlling said automatic analyzing apparatus to temporarily suspend said sample delivery operation in response to said operation interruption request, for controlling said automatic analyzing apparatus to continue said reagent delivery operation to mix necessary kinds of reagents into samples delivered in said reaction containers on said reaction line when said sample delivery operation is temporarily suspended, and for controlling said automatic analyzing apparatus to continue said light-measurement relating to said reaction solution on said reaction line when said sample delivery operation is temporarily suspended;
- a display section for displaying time information representing a time period required for completing delivery of all reagents in said mixing of necessary kinds of reagents after said sample delivery operation is temporarily suspended, said display section displayed on said screen of said display unit; and
- a second operation key for supplying a reagent bottle exchanging work completion signal to said control unit while said reagent bottle exchanging work is possible after completion of an adding operation to add reagents into said samples delivered in said reaction containers, said second operation key being displayed on said screen of said display unit,
- wherein said control unit controls said automatic analyzing apparatus to return to operation from temporary suspension in response to said reagent bottle exchanging work completion signal supplied by said second operation key.

6. An automatic analyzing apparatus according to claim 5, further comprising a read unit for reading identification information of said new reagent bottle in response to said reagent bottle exchanging work completion signal, wherein said control unit restores said automatic analyzing apparatus to said operation state from said temporary suspension state as to said sample delivery operation and said reagent delivery operation after completion of reading of said identification information of said new reagent bottle.

7. An automatic analyzing apparatus according to claim 5, wherein said reagent supply unit includes a reagent disk on which a plurality of reagent bottles are disposed, a movable probe for pipetting reagents within said reaction containers, and a washing solution bottle disposed between said reagent disk and said reaction line, and wherein said control unit washes said movable probe by using said washing solution bottle during said reagent exchange time period.

* * * * *